US00PP37186P2

(12) United States Plant Patent
Ammerlaan

(10) Patent No.: US PP37,186 P2
(45) Date of Patent: Dec. 30, 2025

(54) ***ECHEVERIA* PLANT NAMED 'OVPEARLS16'**

(50) Latin Name: ***Echeveria* hybrid**
Varietal Denomination: OVPEARLS16

(71) Applicant: Ovata B.V., Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 18 days.

(21) Appl. No.: 18/831,545

(22) Filed: Apr. 11, 2025

(51) Int. Cl.
*A01H 5/12* (2018.01)
*A01H 6/32* (2018.01)

(52) U.S. Cl.
USPC ..... Plt./373

(58) Field of Classification Search
USPC ..... Plt./373
See application file for complete search history.

*Primary Examiner* — Susan McCormick Ewoldt
(74) *Attorney, Agent, or Firm* — Samuel R. McCoy, Jr.

(57) ABSTRACT

A new and distinct *Echeveria* hybrid plant named 'OVPEARLS16' which is characterized by having a flattened globular profile with abundant compact foliage that grows erect in the center of the basal rosette and loosens to nearly horizonal as the plant matures. Foliage that is flat, oblong to narrowly obovate with abruptly acute to broad apiculate apices, crenulate foliar margins with heavy undulation, green mature foliage is prominently margined with a translucent light greyed-green color, which transmutes to greyed-purple distally from the base of the lamina, and the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* hybrid disclosed herein has been given the variety denomination 'OVPEARLS16'.

BACKGROUND OF THE INVENTION

Parentage: 'OVPEARLS16' is an interspecific hybrid seedling selection resulting from the controlled pollination of 'ECSIMU-002' *Echeveria elegans* var. *simulans* (Rose) plant (not patented), the seed parent, with 'OVPEARLS08' *Echeveria pulidonis* (U.S. Plant Pat. No. 33,027), the pollen parent. The crossing was made by the inventor in 2020 at a commercial greenhouse in Heerhugowaard, the Netherlands. In 2021, one seedling was observed which exhibited unique growth and foliage characteristics. The seedling was isolated for further evaluation in order to confirm the distinctness and stability of the characteristics first observed. Upon confirmation of distinctness and stability, 'OVPEARLS16' was selected for commercialization.

Asexual Reproduction: Asexual reproduction of the new cultivar 'OVPEARLS16', by way of rooting leaf cuttings, was first initiated in 2021 at the inventor's commercial greenhouse in Heerhugowaard, the Netherlands. Through several subsequent generations, the unique features of this cultivar have proven to be stable and true to type.

SUMMARY OF THE INVENTION

The cultivar 'OVPEARLS16' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'OVPEARLS16'. These characteristics in combination distinguish 'OVPEARLS16' as a new and distinct *Echeveria* hybrid cultivar:

1. 'OVPEARLS16' exhibits a flattened to flattened globular plant profile with abundant compact foliage that grows erect in the center of the basal rosette and loosens to nearly horizontal as the plant matures; and
2. 'OVPEARLS16' exhibits flat, oblong to narrowly obovate foliage with an abruptly acute to broad apiculate apex; and
3. 'OVPEARLS16' exhibits foliar margins that are crenulate with heavy undulation; and
4. 'OVPEARLS16' exhibits green mature foliage that is prominently margined with a translucent light greyed-green color which transmutes to greyed-purple distally from the base of the lamina.

BOTANICAL DESCRIPTION OF THE PLANT

Figure 1:
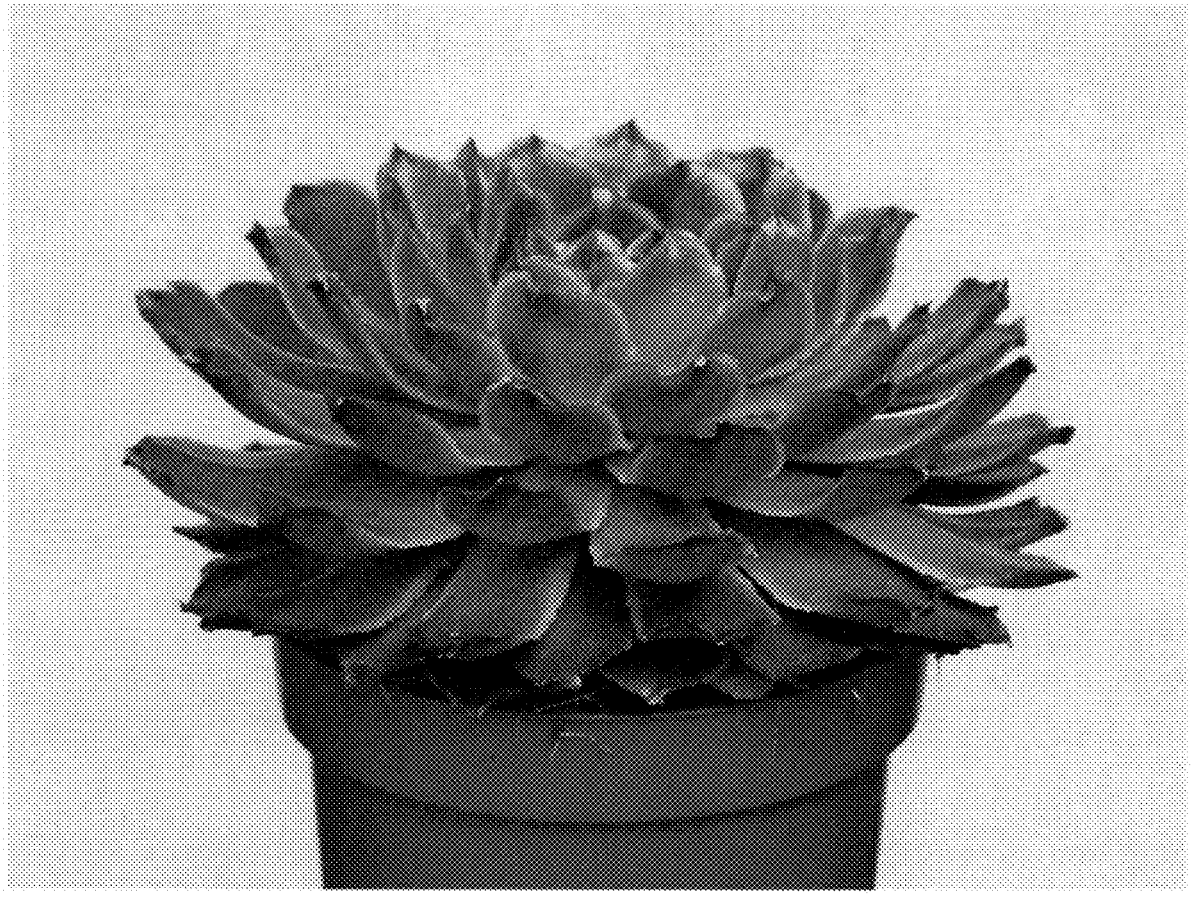
FIG. 1 illustrates, as nearly true as it is reasonably possible to make the same in color photographs of this type, an exemplary plant of 'OVPEARLS16' grown in a commercial greenhouse in Heerhugowaard, the Netherlands. This plant is approximately 12-month-old, shown planted in a 12 cm container.
Figure 2:
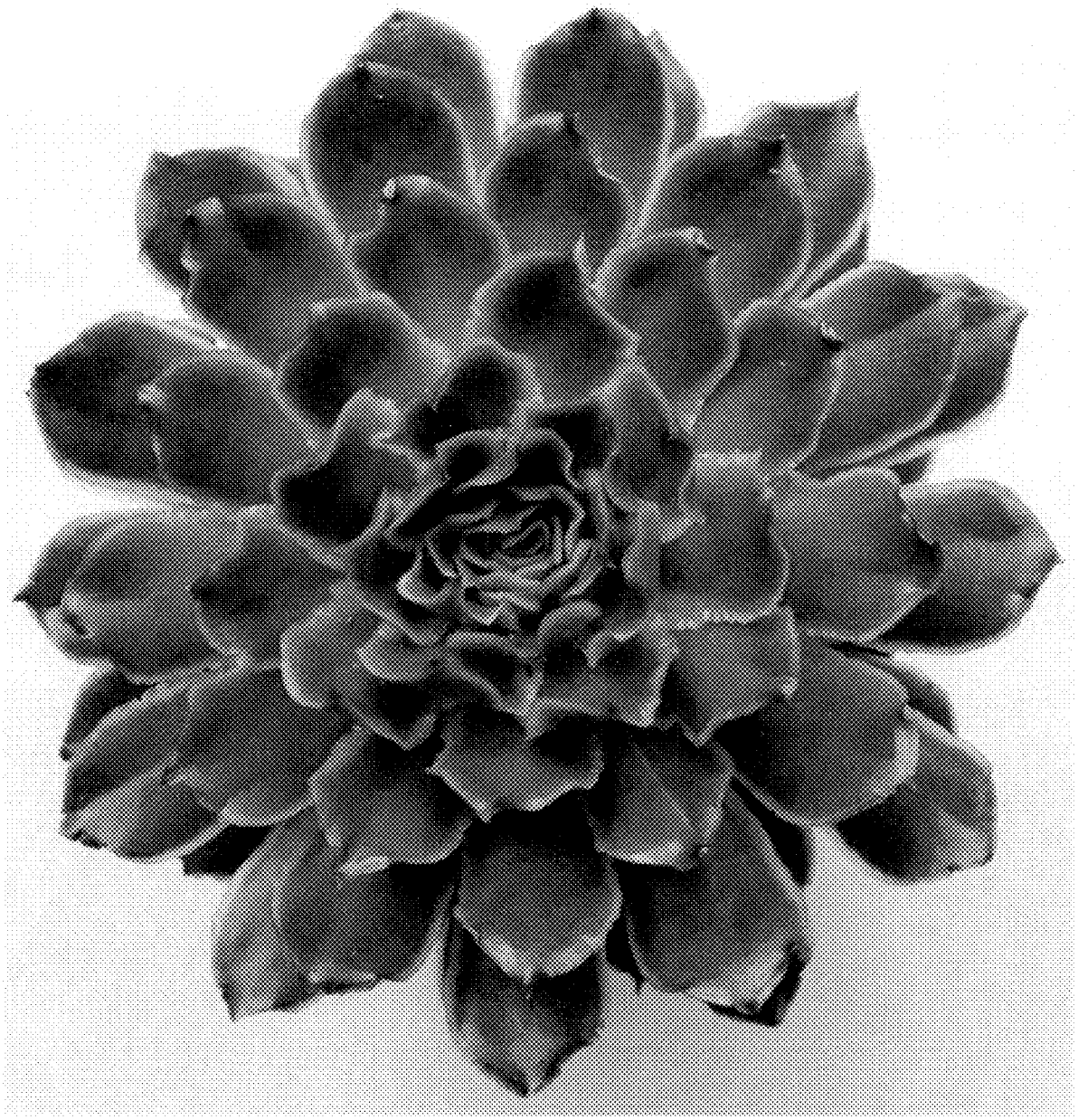
FIG. 2 illustrates, as nearly true as it is reasonably possible to make the same in color photographs of this type, the typical foliage arrangement of 'OVPEARLS16'.
Figure 3:
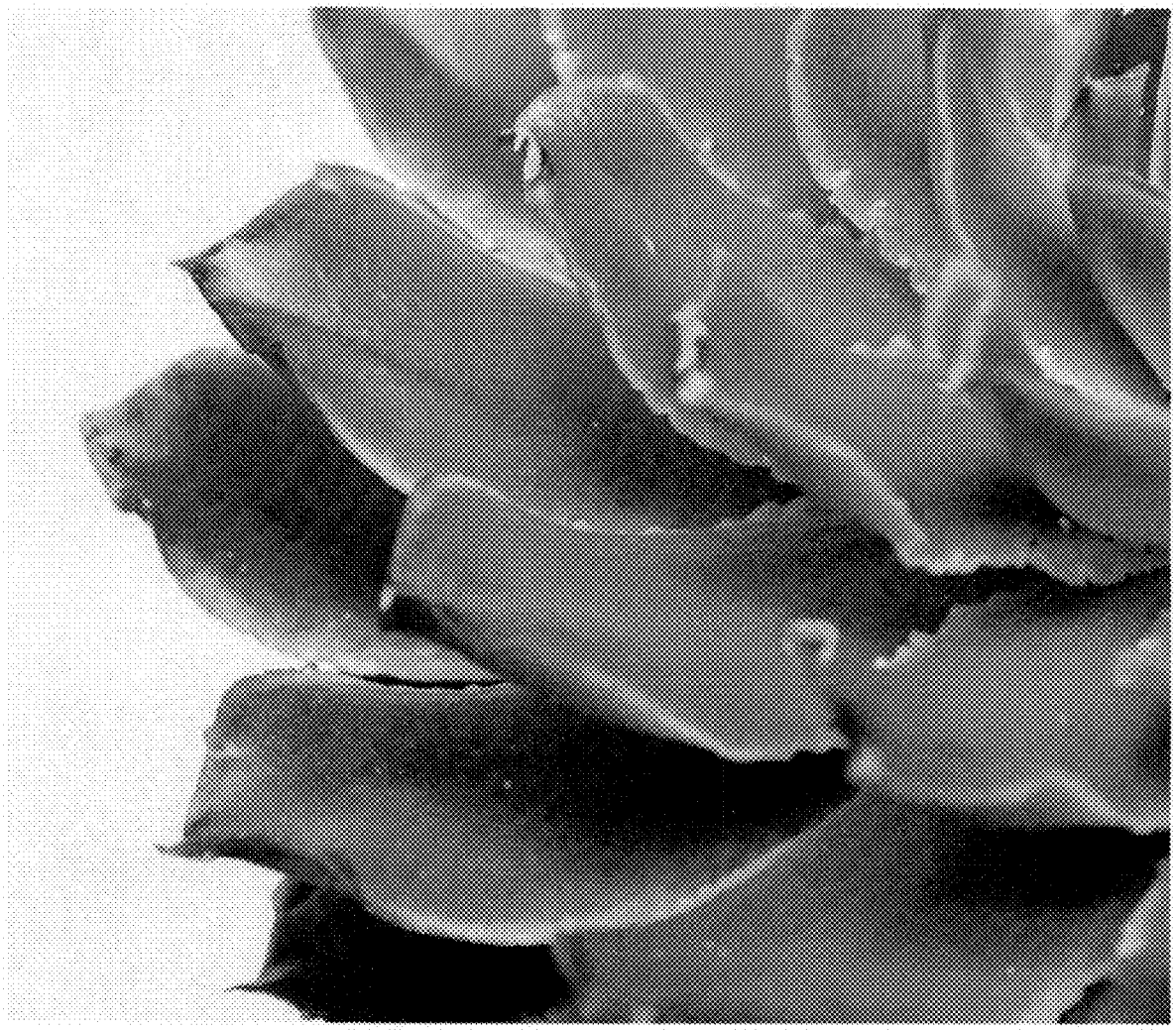
FIG. 3 illustrates, as nearly true as it is reasonably possible to make the same in color photographs of this type, the adaxial surface of the mature foliage 'OVPEARLS16'.
Figure 4:
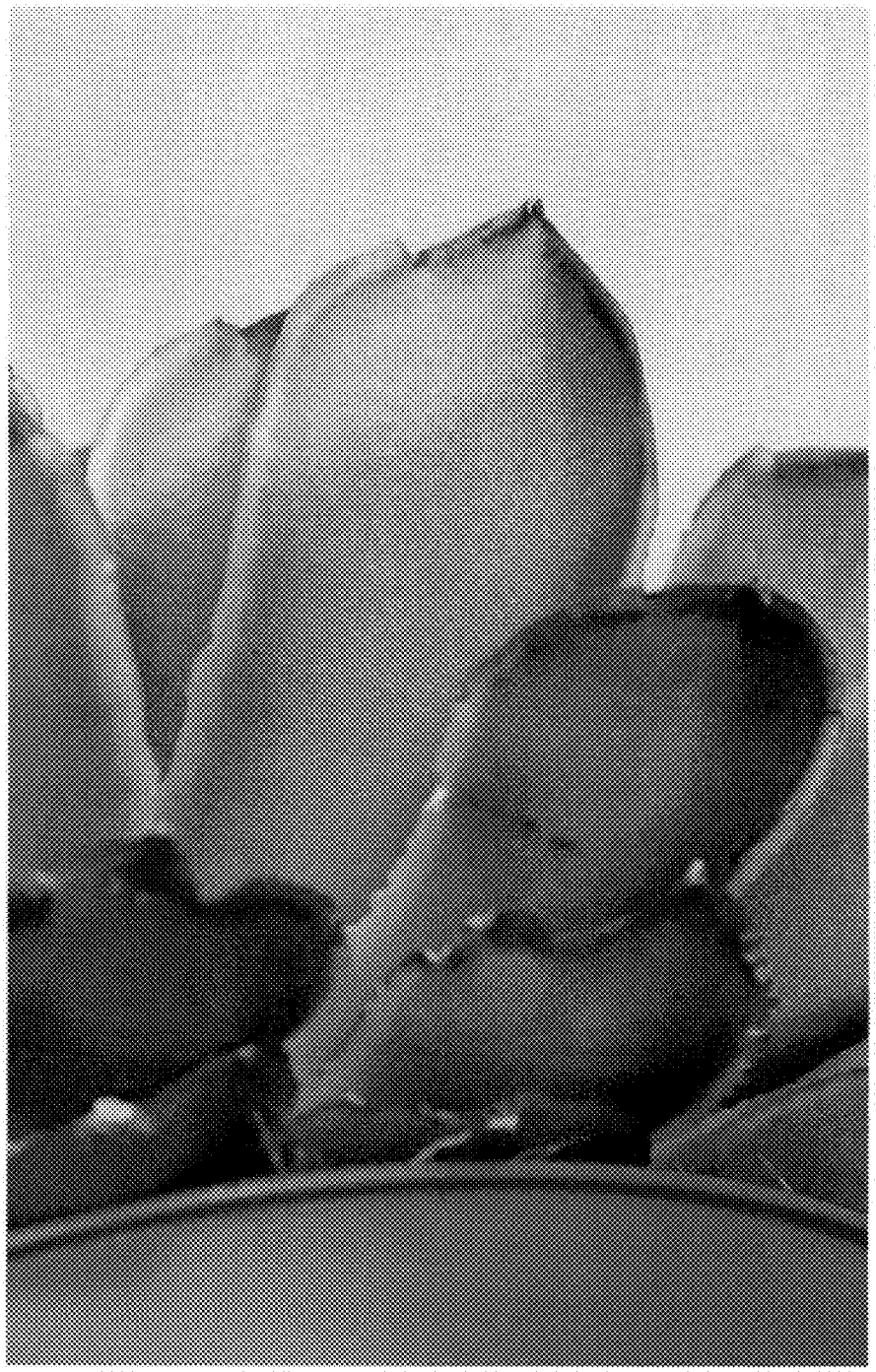
FIG. 4 illustrates, as nearly true as it is reasonably possible to make the same in color photographs of this type, the abaxial surface of the mature foliage 'OVPEARLS16'.

The following observations and measurements made in June of 2021 describe averages from a sample set of six specimens of 12-month-old 'OVPEARLS16' plants grown in 12 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'OVPEARLS16' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'OVPEARLS16' and comparisons with the parent plants and closest known comparator are provided below.

Plant description-

*Growth habit*.—Succulent perennial with foliage growing in a non-branched basal rosette.

*Plant shape*.—Flattened to flattened globular.

*Height from soil level to top of foliar plane*.—7.5 cm.

*Plant spread*.—Average of 17.2 cm.

*Propagation*.—Type — Leaf cuttings. Time to initiate rooting — Approximately 21 days at 18 degrees Celsius. Crop time — Approximately 25 weeks to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosette; no main branches or lateral branches present.

Foliage:

*Arrangement*.—Rosette.

*Division*.—Simple.

*Attachment*.—Sessile.

*Quantity*.—Approximately 100 leaves per rosette.

*Shape*.—Oblong to narrowly obovate.

*Dimensions*.—7.2 cm long, 2.6 cm wide, and 0.7 cm thick, on average.

*Aspect*.—Slightly concave.

*Attitude*.—Juvenile foliage at the center of the rosette is held upright; foliage becomes progressively more relaxed towards the outer whorls of mature foliage; mature foliage is nearly horizontal with leaf tips held at approximately 30 degrees to horizontal.

*Apex*.—Abruptly acute to broad apiculate.

*Base*.—Cuneate.

*Margin*.—Crenulate, heavily undulate.

*Pubescence, texture and luster of the adaxial surface*.—Smooth, glabrous, and glossy succulent leaves.

*Pubescence, texture and luster of the abaxial surface*.—Smooth, glabrous, and glossy succulent leaves.

*Color*.—Juvenile foliage, adaxial surface — Green to yellow-green, nearest to a blend of RHS 137B and 146B, fading to yellow-green, nearest to a combination of RHS 145B and 145C, proximally to the base of the lamina; and narrowly margined with a translucent greyed-green, nearest to RHS 192B, which transmutes to greyed-purple, nearest to RHS 183B, distally from the base of the lamina. Juvenile foliage, abaxial surface — Green, nearest to a blend of RHS 137D and 138B, fading to yellow-green, nearest to RHS 145C, proximally to the base of the lamina; and narrowly margined with a translucent greyed-green, nearest to RHS 192D, which transmutes to greyed-purple, nearest to RHS 184A, distally from the base of the lamina. Mature foliage, adaxial surface — Green, nearest to RHS NN137B, fading to yellow-green, nearest to RHS 145A and 145B, proximally to the base of the lamina; and narrowly margined with a translucent greyed-green, nearest to RHS 192B, which transmutes to greyed-purple, nearest to RHS 183B, distally from the base of the lamina. Mature foliage, abaxial surface — Green, nearest to 138B, fading to yellow-green, nearest to a combination of RHS 145B and 145C, proximally to the base of the lamina; and narrowly margined with a translucent greyed-green, nearest to RHS 192B, which transmutes to greyed-purple, nearest to RHS 183B, distally from the base of the lamina. Venation, adaxial surface — No visible venation. Venation, abaxial surface — No visible venation.

*Petiole*.—No petiole; leaves are sessile.

Inflorescence: No flowering has been observed to date.

COMPARISONS WITH THE PARENT PLANTS AND CLOSEST KNOWN COMPARATOR

Plants of the new cultivar 'OVPEARLS16' differ from the seed parent, *Echeveria elegans* var. *simulans* 'ECSIMU-002' (not patented), in the following characteristics described in Table 1 below.

TABLE 1

Comparison of Characteristics Between 'OVPEARLS16' and 'ESCIMU-002'.

| Characteristic | 'OVPEARLS16' | 'ESCIMU-002' |
|---|---|---|
| Shape and margins of laminas. | Oblong to narrowly obovate shaped laminas that are crenulate with heavy undulation. | Spathulate shaped laminas that are less crenulate than 'OVPEARLS16'. |
| General coloration of the foliage. | Darker green than 'ESCIMU-002' with translucent greyed-green margins that transmutes to greyed-purple towards the laminar tips. | Light Green with greyed-green margins with a red overtone along the tips of the lamina. |

Plants of the new cultivar 'OVPEARLS16' differ from the pollen parent, *Echeveria pulidonis* 'OVPEARLS08' (U.S. Plant Pat. No. 33,027), in the following characteristics described in Table 2 below.

TABLE 2

Comparison of Characteristics Between 'OVPEARLS16' and 'OVPEARLS08'.

| Characteristic | 'OVPEARLS16' | 'OVPEARLS08' |
|---|---|---|
| Abundance of foliage. | More abundant and compact than 'OVPEARLS08'. | Less abundant than 'OVPEARLS16' and loose plant profile. |
| Growing habit. | More relaxed than 'OVPEARLS08', maturing to nearly horizontal. | Nearly upright and strongly concave foliage. |
| General coloration of the foliage. | Green with greyed-green to greyed-purple margins. | Yellow-green with strong suffusion of purple on the surface of the lamina and margins. |
| Foliar margins. | Crenulate; heavily undulated. | Entire; not undulated. |
| Laminar apices. | Abruptly acute to broad apiculate. | Acute to mucronate. |

COMPARISONS WITH THE CLOSEST KNOWN COMPARATOR

Plants of the new cultivar 'OVPEARLS16' differ from the closest known commercial comparator, *Echeveria agavoides* 'Fiesta' (not patented), in the following characteristics described in Table 3 below.

TABLE 3

Comparison of Characteristics Between 'OVPEARLS16' and 'Fiesta'

| Characteristic | 'OVPEARLS16' | 'Fiesta' |
|---|---|---|
| Abundance of foliage. | More abundant and compact than 'Fiesta'. | Less abundant than 'OVPEARLS16' and loose plant profile. |
| General coloration of the mature foliage. | A darker green than 'Fiesta' with no epicuticular wax present. | Pale greyed-green with a slight cyanic hue. |
| Foliage margins. | Oblong to narrowly obovate shaped laminas that are crenulate with heavy undulation. | Spathulate shaped laminas that are entire and non-undulated. |
| Distal portion of the leaf margins. | Margined with a translucent greyed-green which transmutes to greyed-purple. | Margined greyed-green, generally appearing red at the distal most point. |
| Laminar apices. | Abruptly acute to broad apiculate. | Acute to mucronate. |

That which is claimed is:

1. A new and distinct variety of *Echeveria* hybrid plant named 'OVPEARLS16', substantially as described and illustrated herein.

* * * * *